United States Patent [19]

Lilje

[11] Patent Number: 4,663,452

[45] Date of Patent: May 5, 1987

[54] THIATION PROCESS

[75] Inventor: Kenneth C. Lilje, Baton Rouge, La.

[73] Assignee: Ethyl Corporation, Richmond, Va.

[21] Appl. No.: 770,603

[22] Filed: Aug. 29, 1985

[51] Int. Cl.$^4$ .......................................... C07D 267/14
[52] U.S. Cl. .................................. 540/490; 540/488; 560/16; 560/10; 568/20; 558/230
[58] Field of Search .................. 260/239.8 B; 564/74, 564/78; 560/16, 10

[56] References Cited

U.S. PATENT DOCUMENTS 4,439,617  3/1984  Sestanj et al. ......................... 560/39

FOREIGN PATENT DOCUMENTS 107930  5/1984  European Pat. Off. ..... 260/239.3 B
741109 11/1943  Fed. Rep. of Germany ........ 564/78

OTHER PUBLICATIONS

Scheeren et al., "Synthesis" (1973) pp. 149–151.

Primary Examiner—Robert T. Bond
Attorney, Agent, or Firm—Donald L. Johnson; John F. Sieberth; Patricia J. Hogan

[57] ABSTRACT

An organic carbonyl compound is thiated to the corresponding thiono compound by reacting it with phosphorus pentasulfide in the presence of an alkali metal bicarbonate and a hydrocarbon diluent. In preferred embodiments of the invention, the carbonyl compound is an amide, especially an aromatic amide, and the diluent is an inert hydrocarbon having a boiling point in the range of about 50°–150° C.

13 Claims, No Drawings

THIATION PROCESS

FIELD OF INVENTION

This invention relates to thiono compounds and more particularly to a process for preparing such compounds by the thiation of the corresponding carbonyl compounds.

BACKGROUND

As disclosed in U.S. Pat. No. 4,439,617 (Sestanj et al.), European Patent Application No. 0107930 (Cale et al.), and Scheeren et al., *Synthesis*, 1973, pp. 149–151, it is known that carbonyl compounds can be converted to the corresponding thiono compounds by reaction with tetraphosphorus decasulfide (more commonly, though less accurately, known as phosphorus pentasulfide). Scheeren et al. teach that improved results can be obtained by conducting such thiations in the presence of sodium bicarbonate and a polar solvent, and they also teach that their improved process is believed to be accomplished by a mechanism which would require the presence of their polar solvent.

SUMMARY OF INVENTION

An object of this invention is to provide a novel process for thiating carbonyl compounds.

Another object is to provide such a process that does not require the use of a polar solvent.

A further object is to provide such a process that is capable of producing thiono compounds in higher yields.

These and other objects are attained by reacting an organic carbonyl compound with phosphorus pentasulfide in the presence of an alkali metal bicarbonate and a hydrocarbon diluent so as to convert the carbonyl group to a thiono group.

DETAILED DESCRIPTION

The carbonyl compound that is used in the practice of the invention may be any organic carbonyl compound that is thiatable with phosphorus pentasulfide, e.g., an aliphatic, cycloaliphatic, aromatic, or heterocyclic aldehyde, ketone, amide, ester, or thioester. Such compounds, of course, are already known and include, e.g., acetaldehyde, hexaldehyde, benzaldehyde, acetone, benzophenone, 4,4'-dimethoxybenzophenone, di-tolyl ketone, di-(p-dimethylaminophenyl) ketone, t-butyl p-methoxyphenyl ketone, acetophenone, xanthone, ethyl formate, ethyl acetate, methyl cyclohexanoate, methyl thioacetate, ethyl thiobenzoate, imidazolone, formamide, acetamide, propionamide, phenylacetamide, N-methyl phenylacetamide, N-(3,4-dimethoxyphenyl)acetamide, N,N-dimethylformamide, N-(p-chlorophenyl)acetamide, p-nitrobenzamide, N-phenyl-p-aminobenzamide, N-phenyl-p-dimethylaminobenzamide, saccharamide, camphorimide, methyl N-[(6-methoxy-5-trifluoromethylnaphthalenyl)carbonyl]-N-methylaminoethanoate, 2-(2-chloroethyl)-2,3-dihydro-4-methyl-1,4-benzoxazepin-5(4H)-one, 2-(2-chloroethyl)-2,3-dihydro-4-methylpyrido[3,2-f]-1,4-oxazepin-5(4H)-one, 2-(2-chloroethyl)-2,3-dihydro-4-methylnaphth[2,3-f]-1,4-oxazepin-5(4H)-one, etc.

In a preferred embodiment of the invention, the carbonyl compound is an amide, especially an aromatic amide. In a particularly preferred embodiment, it is an alkyl or aralkyl N-[(6-alkoxy-5-trifluoromethylnaphthalenyl)carbonyl]-N-alkylaminoethanoate wherein the alkyl groups contain 1–6 carbons, such as the amidoesters of Sestanj et al., the teachings of which are incorporated herein by reference. In another particularly preferred embodiment, the carbonyl compound is an aromatic 2,3-dihydro-1,4-oxazepin-5(4H)-one such as those taught in Cale et al. (the teachings of which are incorporated herein by reference) and including, e.g., 2-(2-haloethyl)-2,3-dihydro-1,4-benzoxazepin-5(4H)-ones, 2-(2-haloethyl)-2,3-dihydro-4-alkylpyrido[3,2-f]-1,4-oxazepin-5(4H)-ones, etc., especially those substituted with an alkyl or aralkyl group in the 4-position.

The phosphorus pentasulfide, as indicated above, is the thiating agent that is also known as tetraphosphorus decasulfide. It is preferably employed in substantially pure form and is used in at least the stoichiometric amount, generally in excess of that amount. There is no maximum to the amount that may be employed except for the maximum that might be set by economic considerations. Most commonly, the sulfide is used so as to provide at least one atom, preferably at least about two atoms, of sulfur per carbonyl group.

The alkali metal bicarbonate employed in the reaction may be any such bicarbonate but is generally lithium, sodium, or potassium bicarbonate, most commonly sodium bicarbonate. It is used so as to provide at least one, preferably at least about two, bicarbonate radicals per carbonyl group. There is no apparent maximum to the amount that may be used.

The diluent is an inert normally liquid hydrocarbon which may be aliphatic, cycloaliphatic, or aromatic and is preferably a hydrocarbon having a boiling point of at least about 50° C., most commonly about 50°–150° C. Hydrocarbons having higher of lower boiling points may be used if desired. However, since the significance of the boiling point is that the reaction is most conveniently conducted at the boiling point of the diluent, the use of a lower boiling hydrocarbon generally leads to a slower reaction, and the use of a hydrocarbon having too high a boiling point could lead to decomposition of the product or a starting material. Examples of hydrocarbons that can be used as the diluent include hexane, heptane, octane, nonane, decane, cyclopentane, cyclohexane, cycloheptane, benzene, toluene, xylene, etc., as well as less easily available liquid hydrocarbons. It is generally preferred to employ an aromatic hydrocarbon, such as toluene. However, since the hydrocarbon functions as a diluent for a heterogeneous reaction mixture in the present invention, its particular nature is less significant than would be the case if its function were to solvate the other ingredients.

The reaction is conducted by combining the aforementioned ingredients of the reaction mixture and heating them at a suitable temperature, preferably reflux temperature until a substantial amount of the carbonyl compound has been converted to the corresponding thiono compound. The time required for the reaction varies with the particular starting materials and temperature employed but is frequently about 1–5 hours. Yields may be improved by employing anhydrous starting materials and reaction conditions. In a preferred embodiment of the invention, the reaction is conducted by preslurrying the phosphorus pentasulfide and alkali metal bicarbonate in at least a portion of the diluent, then adding the carbonyl compound (preferably as a solution in a portion of the diluent) with agitation, and heating the reaction mixture at reflux temperature until a substantial amount of the carbonyl compound has been converted to the corresponding thiono compound. Best results are obtained when the slurry of sulfide and bicarbonate is preheated to a temperature close to the boiling point of the diluent for a suitable time, e.g., about 15-45 minutes, before the carbonyl compound is added.

After completion of the reaction, the product may be recovered by conventional means. However, work-up is facilitated when the product is recovered by adding a demulsifier (i.e., an emulsion breaker) to the thiono compound-containing reaction mixture at a temperature at which the demulsifier is liquid, subsequently adding water, and stirring for a time sufficient to achieve adequate admixture of the reaction mixture, demulsifier, and water prior to separating an organic phase and evaporating it to isolate the product. The demulsifier may be any material capable of changing the surface tension but is most suitably an alcohol, e.g., ethanol, or an ether, e.g., tetrahydrofuran. The best conditions for this procedure vary with the particular reaction mixture being worked up. However, in the case of an aromatic 2,3-dihydro-1,4-oxazepine-5(4H)-thione that has been prepared in toluene, it has been found that excellent results are obtained by cooling the reaction mixture to the boiling point of the demulsifier (e.g., tetrahydrofuran), adding about two parts by weight of demulsifier for each part of carbonyl compound that was used initially, cooling to room temperature, adding about one part by weight of water for each part of the initial carbonyl compound, and stirring for about 1-3 hours before separating out the various ingredients of the reaction mixture.

The invention is advantageous as a means of producing thiono compounds from carbonyl compounds in higher yields and shorter times than are achieved in the solution process of Scheeren et al. The products can be recovered by the use of a simple work-up procedure, and the process typically gives a crude product that is more than 90% pure.

The following examples are given to illustrate the invention and are not intended as a limitation thereof. In these examples the term "phosphorus pentasulfide" is used to denote the compound having the formula $P_4S_{10}$, "Amide" is used to denote 2-(2-chloroethyl)-2,3-dihydro-4-methylpyrido[3,2-f]-1,4-oxazepin-5-(4H)-one, and the "desired thioamide" refers to the thione corresponding to the Amide.

COMPARATIVE EXAMPLE A

To 70 mL of toluene in a nitrogen atmosphere were added 9.8 g (22.14 mmols) of phosphorus pentasulfide. The suspension was warmed to 90° C., and a solution of 7.39 g (30.7 mmols) of Amide in 10 mL of toluene was added dropwise. The resulting suspension was heated to reflux. After three hours at reflux, thin layer chromatography (tlc) showed the starting material to be substantially gone, and the heat was removed. The reaction mixture was then filtered. The filtrate was washed with 10 mL of saturated sodium bicarbonate solution. The organic phase was dried over magnesium sulfate, filtered, and concentrated, giving 4.55 g of crude product (58% mass yield). The solids from the initial filtration were treated with saturated sodium bicarbonate and toluene. This mixture was then filtered through Celite. The organic phase was dried over magnesium sulfate, filtered, and evaporated, giving 1.5 g of crude product. The total amount of the desired thioamide obtained as crude product was 6.05 g (77% theoretical mass).

EXAMPLE I

To 70 mL of toluene under nitrogen were added 4.1 g (9.25 mmols) of phosphorus pentasulfide and 7.76 g (92.46 mmols) of sodium bicarbonate. The resulting suspension was warmed to 90° C. and stirred for 30 minutes. To the resulting suspension were added 41.3 g of a toluene solution containing 11.5 g (47.8 mmols) of Amide dropwise over 40 minutes. The resulting mixture was heated to reflux. After one hour, tlc showed the starting material gone. The heat was removed and 25 mL of tetrahydrofuran were added to the warm suspension. After the mixture had cooled to ambient temperature, 11 mL of water were added, and stirring was continued for three hours. The resulting suspension was filtered. The organic phase in the filtrate was separated and evaporated, leaving 13.95 g of crude product. Preparative tlc showed this to contain 11 g of the desired thioamide (90% yield).

EXAMPLE II

A mixture of 2.9 g (6.65 mmols) of phosphorous pentasulfide, 5.5 g (66 mmols) of sodium bicarbonate, and 75 mL of toluene was refluxed under nitrogen for 45 minutes. To the refluxing suspension were added 18 g of a solution containing 8 g (33.26 mmols) of Amide. After one hour, tlc showed the starting material to be completely gone. The heat was removed and 16 mL of THF added. On cooling, 10 mL of ethanol and 8 mL of water were added. After three hours the mixture was filtered. The phases were separated and the organic phase evaporated, giving 8.56 g of crude product. Preparative tlc showed this to contain 8.08 g of the desired thioamide (95% yield).

EXAMPLE III

A mixture of 2.9 g (6.65 mmols) of phosphorus pentasulfide, 5.5 g (66 mmols) of sodium bicarbonate, and 75 mL of toluene was heated to reflux. After 20 minutes, 18 g of a toluene solution containing 8 g (33.26 mmols) of Amide were added. After one hour, tlc showed the reaction to be complete, so the heat was removed. After cooling, 8 g of ethanol and 8 g of water were added. After stirring for two hours, the mixture was filtered and the phases separated. The organic phase was evaporated, giving 8.93 g of crude product. Preparative tlc showed this to contain 7.44 g of the desired thioamide (88% yield).

EXAMPLE IV

To 40 mL of toluene under nitrogen were added 2.78 g (6.28 mmols) of phosphorus pentasulfide and 6.5 g (62.8 mmols) of potassium bicarbonate. The mixture was warmed, and 50 g of a toluene solution containing 7.55 g (31.4 mmols) of Amide were added. The suspension was heated to reflux. After one hour, tlc showed the starting material gone, and the heat was removed. After cooling, 6.5 g of additional potassium bicarbonate and 50 mL of water were added and the mixture stirred overnight. The resulting suspension was filtered through Celite. The organic phase was separated, dried over magnesium sulfate, and evaporated, giving 6.75 g of crude product. Preparative tlc showed this to contain 4.13 g of the desired thioamide (51% yield).

It is obvious that many variations can be made in the products and processes set forth above without departing from the spirit and scope of this invention.

What is claimed is:

1. A process which comprises reacting an amide with phosphorus pentasulfide in the presence of an alkali metal bicarbonate and a hydrocarbon diluent so as to convert the carbonyl group of the amide to a thiono group.

2. The process of claim 1 wherein the amide is an aromatic amide.

3. The process of claim 2 wherein the aromatic amide is an aromatic 2,3-dihydro-1,4-oxazepin-5(4H)-one.

4. The process of claim 2 wherein the aromatic amide is an N[(6-alkoxy-5-trifluoromethylnaphthalenyl)carbonyl]-N-alkylaminoethanoate ester.

5. The process of claim 1 wherein the alkali metal bicarbonate is sodium bicarbonate.

6. The process of claim 1 wherein the diluent is an inert hydrocarbon having a boiling point in the range of about 50°–150° C.

7. The process of claim 6 wherein the diluent is an aromatic hydrocarbon.

8. The process of claim 7 wherein the aromatic hydrocarbon is toluene.

9. The process of claim 1 wherein the reaction is conducted by adding a solution of the amide in a portion of the hydrocarbon diluent to an agitated slurry of the phosphorus pentasulfide and alkali metal bicarbonate in the remainder of the hydrocarbon diluent and heating the reaction mixture at reflux temperature until a substantial amount of the amide has been converted to the corresponding thiono compound.

10. The process of claim 1 wherein the thiono compound formed by the reaction is recovered by adding a demulsifier to the thiono compound-containing reaction mixture at a temperature at which the demulsifier is liquid, subsequently adding water, and stirring for a time sufficient to achieve adequate admixture of the reaction mixture, demulsifier, and water prior to separating out an organic phase and evaporating it to isolate the product.

11. The process of claim 10 wherein the demulsifier is an ether or alcohol.

12. A process which comprises reacting 2-(2-chloroethyl)-2,3-dihydro-4-methylpyrido[3,2-f]-1,4-oxazepin-5(4H)-one with phosphorus pentasulfide in the presence of an alkali metal bicarbonate and a hydrocarbon diluent so as to convert the carbonyl group of the oxazepinone to a thiono group.

13. The process of claim 9 wherein the pentasulfide/bicarbonate slurry is heated before the amide solution is added thereto.

* * * * *